US006322803B1

(12) United States Patent
Van Voris et al.

(10) Patent No.: US 6,322,803 B1
(45) Date of Patent: Nov. 27, 2001

(54) METHOD FOR APPLYING PESTICIDES AND REPELLENTS

(75) Inventors: Peter Van Voris, Richland; Dominic A. Cataldo, Kennewick, both of WA (US); Edward S. Lipinsky, Worthington, OH (US)

(73) Assignee: Bioguard Technologies, Inc., Kennewick, WA (US)

( * ) Notice: Subject to any disclaimer, the term of this patent is extended or adjusted under 35 U.S.C. 154(b) by 0 days.

(21) Appl. No.: 09/347,704

(22) Filed: Jul. 3, 1999

(51) Int. Cl.[7] .................................................... A01N 25/32

(52) U.S. Cl. ......................... 424/406; 424/46; 424/78.37; 424/408; 424/409; 424/419; 424/DIG. 11; 514/124; 514/531

(58) Field of Search .................................... 424/406, 407, 424/409, 411, 408, 419, 78.08, 78.09, 78.18, 78.31, 78.35, DIG. 11, 46, 78.36, 78.37; 514/919, 531, 124; 427/447, 487

(56) References Cited

U.S. PATENT DOCUMENTS

| | | | | |
|---|---|---|---|---|
| 2,899,771 | | 8/1959 | Burris . | |
| 3,705,938 | | 12/1972 | Hyman . | |
| 4,102,991 | | 7/1978 | Kydonieus . | |
| 4,103,450 | | 8/1978 | Whitcomb . | |
| 4,160,335 | | 7/1979 | Von Kohorn . | |
| 4,190,680 | | 2/1980 | Young . | |
| 4,198,441 | | 4/1980 | Young . | |
| 4,198,782 | | 4/1980 | Kydonieus . | |
| 4,235,872 | | 11/1980 | Tocker . | |
| 4,282,209 | | 8/1981 | Tocker . | |
| 4,400,374 | | 8/1983 | Cardarelli . | |
| 4,405,360 | | 9/1983 | Cardarelli . | |
| 4,435,383 | | 3/1984 | Wysong . | |
| 4,666,767 | | 5/1987 | Von kohorn . | |
| 5,139,566 | | 8/1992 | Zimmerman . | |
| 5,359,806 | | 11/1994 | Jeffrey . | |
| 5,576,008 | * | 11/1996 | Yang et al. | 424/408 |
| 5,801,194 | * | 9/1998 | Van Voris et al. | 514/531 |
| 5,856,271 | | 1/1999 | Cataldo . | |
| 5,860,266 | | 1/1999 | Martinet . | |
| 5,985,304 | * | 11/1999 | Van Voris et al. | 424/406 |
| 6,033,681 | * | 3/2000 | Narayanan et al. | 424/405 |
| 6,048,892 | * | 4/2000 | Iwasaki et al. | 514/461 |
| 6,099,850 | * | 8/2000 | Van Voris et al. | 424/411 |

FOREIGN PATENT DOCUMENTS

| | | | |
|---|---|---|---|
| B-82443/91 | | 2/1992 | (AU) . |
| 58-43050 | * | 9/1983 | (JP) . |
| 62 236937 | * | 10/1987 | (JP) . |

OTHER PUBLICATIONS

G. Oertel, Polyurethane Handbook, 2d edition, 1993, pp. 216–217, 209–210, 115–116, Hanser Gardner Publications, Inc., Cincinnati, OH, USA.

H.B. Scher, et al., "Microencapsulation of Pesticides by Interfacial Polymerization Utilizing Isocyanate or Aminoplast Chemistry," Pesticide Science 1998, 54, pp. 394–400.

* cited by examiner

*Primary Examiner*—Neil S. Levy
(74) *Attorney, Agent, or Firm*—Mueller and Smith, LPA

(57) ABSTRACT

A method for creating an wood destroying organism resistant coating is disclosed. The method involves spraying a structure with a mixture of a quick setting liquid monomer and a pesticide. The monomer, when cured, forms a bonded polyurethane coating upon the surface a structure which slowly releases pesticide over long periods of time. The method may be practiced as a two part system utilizing monomers and catalytic curing agents, and a one part system utilizing masked isocyanates.

13 Claims, No Drawings

METHOD FOR APPLYING PESTICIDES AND REPELLENTS

FIELD OF THE INVENTION

The present invention relates generally to a method for applying and delivering pesticides, insecticides and repellents to structures. More specifically, the present invention relates to systems utilizing pressurized spraying to form a coating of a long lasting adhesive bonding material containing a pesticide in two forms in either a single or two part delivery system.

BACKGROUND OF THE INVENTION

Wood and wood products utilized in a variety of construction applications are frequently structurally degraded by the action of termites, ants, other boring insects and wood decaying microorganisms. Typically, these wood degrading and decaying organisms migrate to wood structures via the surrounding soils. This migration may occur whether the structures rest upon concrete foundations, such as in wooden building construction, or if the structures are in direct contact with soil, for example fence posts, utility poles, railroad cross-ties, pier pilings, wooden docks, wooden supports and like structures.

Present methods of preventing or retarding the advance of these wood degrading organisms include both soil treatment with pesticides and repellent chemicals, treating the wood with chemicals, and fumigation wherein the entire structure may be sealed and a pesticide, insecticide or repellent released. Both soil and fumigation type treatments may release the pesticide, insecticide or repellent to the surrounding atmosphere or move to ground water where it may harm human beings or other living organisms. Disadvantages of these methods of treating soil and/or fumigating include potential ecological and human health concerns as well as the limited time until the fumigant or soil concentration is sufficiently reduced in concentration to permit ingress of wood degrading organisms.

Although many pesticides and repellent are known to be effective against the action of wood destroying organisms, their effectiveness often declines over time as they are dissipated into the surrounding environment (soil or atmosphere) or are degraded either chemically or biologically. To retain their effectiveness, these insecticides must therefore be repeatedly applied at regular intervals ranging from every few days to a few months or a few years. Alternatively, if these pesticides and repellents are applied in sufficient quantity to be effective over a period of time, the ecological and human health related concerns associated with these chemicals and the unpleasant odors are exacerbated. Furthermore, with the banning of certain chemicals and the introduction of safer shorter half-life compounds, even large amounts of many of these pesticides and repellents may be required over a relatively short time periods, and they will need to be reapplied more often.

A further disadvantage of conventional application methods is that the concentration of pesticides and repellents resulting from a single application starts out well above the minimum concentration necessary for effectiveness, but decreases rapidly. Within a relatively short period of time that concentration drops below the minimal effective level necessary to maintain a barrier to the invasion of wood destroying organisms.

To overcome these problems, a number of techniques for the controlled release of chemicals such as insecticides have been proposed in recent years. These methods employ polymer matrices and microcapsules used to contain insecticide and allow the slow release of the pesticides and repellents over extended time periods. One such scheme is found in U.S. Pat. No. 4,400,374 to Cardarelli which discloses the use of polymer matrices generally made of polyethylene, polypropylene, ethylene vinyl acetate, polyamide, polystyrene, polyvinyl acetate, or polyurethane to control the release of insecticides such as the insecticide commercially available under the tradename Dursban. The polymer matrices disclosed in U.S. Pat. No. 4,400,374, incorporate porosigen and a porosity reducing agent which upon contact with soil moisture or an aqueous environment dissolves the matrix.

Similarly, Cardarelli U.S. Pat. No. 4,405,360 relates to a polymer release matrix which can be composed of polyamide, polyurethane, polyethylene, polypropylene, polystyrenes and other polymers. The control release mechanism works in combination with a porosigen to release a herbicide in a moist environment.

A disadvantage of the Cardarelli methods is the necessity of sufficient moisture to dissolve the matrix. Periods of dryness, while extending the life of the matrix, would result in a decrease in the insecticide concentration thereby permitting insects to have access to the wooden structure. In addition, the longevity of the matrix is variable and dependent upon moisture content.

In addition, Wysong U.S. Pat. No. 4,435,383 teaches the use of a controlled release mechanism for insecticides including carbamates, organothiophosphates, organophosphates, perchlorinated organics and synthetic pyrethroids. The release mechanism comprises a hydrophobic barrier that is a polymer prepared from a monomer namely styrene and/or methyl styrene in combination with a monomer selected from one or more unsaturated mono- or di-carboxylic acids.

Martinet U.S. Pat. No. 5,860,266 describes the preparation of construction sites with plastic sheets impregnated with an insecticide.

Another reference, Tocker U.S. Pat. No. 4,282,209 discusses a process for the preparation of insecticide-polymer particles. The insecticide, methomyl, is used to control insects which attack a tobacco, cotton or other agricultural crops. Methomyl is dissolved with polymers such as polyamides, urethanes, and epoxies to provide extended residual insecticidal activity.

A second Tocker patent, U.S. Pat. No. 4,235,872, discloses the use of slow-release insecticide microcapsules having a core of methomyl surrounded by a cover of all-aromatic, uncrosslinked polyurea. In the arrangement disclosed in this patent, methomyl is used to protect vegetables, field crops, and fruit crops.

A sixth reference, Young et al. U.S. Pat. No. 4,198,441, discloses the use of insecticides such as chlorpyrofos, tradenamed Dursban, in a controlled release matrix comprising an organopolysiloxane, a hydrolyzable silane and a hydrolyzable organic titanium compound.

Additionally, Young et al. U.S. Pat. No. 4,160,335 discloses a mode of dispersing insect control substances by applying stripes to sheets of cellophane. The insect control substance which can include Dursban is placed in a polymer as well.

Another method is described in an Australian patent AU-B-82443/91. In this patent, there is described two sheets of plastic drawn from supply rolls. The upper face of the lower sheet and the lower face of the upper sheet are drawn past respective coating rollers which apply a coating of pesticide (e.g. permethrin) in a volatile solvent to the faces of the sheets. The coated faces of the sheets are brought together by passing them between compressive rollers. The coated and pressed sheets are laid under building foundations, or placed around trees or plants to prevent termite attack. Disadvantages of this product and method include (1) delamination of a layer permits rapid escape of the coating, and (2) the coating is not integral to the sheets thereby permitting faster diffusion through the sheets and limiting the effective life.

Coated granules have a pesticide absorbed onto a matrix such as clay and then coated with cross-linked resins which helps slow the release rate. Clay loses or releases pesticide over a short period of at most a few weeks.

In U.S. Pat. No. 5,801,194 to Van Voris et al., (the '194 patent) a controlled release device is disclosed which incorporates insecticide into polymer materials to form a device which may then be placed in and around wooden structures to form an effective exclusion zone lasting several years or more. This is accomplished through the use of a low volatility insecticide within a high density polymer, the combination having a low release rate of the insecticide. While the '194 patent does describe a device which provides long lasting protection against insect penetration, the application of this device to either new or existing structures requires the manual placement of the device in and around those structures. The application of the device in this manner may be time consuming, labor intensive, and expensive. In one embodiment of the '194 patent, the controlled release device is placed into a polyurethane foam to allow the spray application of the device to wooden structures. While this approach does lessen the labor, and thus the cost, associated with placing the device in contact with the structures that need to be protected, it does have other drawbacks. For example, at the time the device is applied to the structure, the insecticide is not adequately dispersed throughout the volume of the polyurethane foam. This results in a lack of protection from invasive insects during the time period required for the insecticide to permeate the polymer and infiltrate the foam. To overcome this drawback, the '194 patent also proposes combining the low volatility insecticide within a high density polymer with a more volatile insecticide within a low density polymer which has a higher release rate. The drawbacks of this combined system include the potential harm to human and other life forms which may occur as a result of their coming into contact with the more volatile insecticide.

Thus, there exists a need for improved methods for applying a pesticide or repellent barrier to wooden structures which provides long lasting and immediate protection from termites, ants, wood boring insects and other wood destroying microorganisms as well as provides a protective barrier against the migration of the pesticide, insecticide or repellent into the environment where it can potentially cause adverse ecological and human health impacts. There exists a particular need for methods for applying such barriers which may be accomplished quickly and inexpensively. Finally, there exists a need for methods which accomplish the foregoing objectives in a manner which minimizes the opportunity for the pesticide, insecticide or repellent to come into contact with humans or other living creatures which may be harmed by such contact.

OBJECTS

Accordingly, it is an object of the present invention to provide an inexpensive convenient method for applying a pesticide, insecticide or repellent which protects wooden structures.

It is a further object of this invention to provide this protection of the wooden structures for relatively great lengths of time of from 1 to more than 30 years.

It is a further object of this invention to provide this protection in a manner that provides protection to the structures immediately upon the application of the delivery device for the pesticide, insecticide or repellent.

It is a further object of this invention to provide immediate protection without allowing the release of the pesticide, insecticide or repellent to the environment in quantities which may have the potential to harm human beings or other desirable life forms which may come into contact with the wood destroying or wood decaying barrier.

It is a further object of this invention to provide the pesticide, insecticide or repellent within a protective coating of polyurethane which has been bonded to the protected structures.

It is a further object of this invention to provide this protective coating by spraying a mixture of the pesticide, insecticide or repellent with a suitable monomer.

It is a further object of this invention to provide this protective coating by spraying a mixture of the pesticide, insecticide or repellent with a suitable monomer with spraying equipment which utilizes pressurized gas or air to spray the monomer.

It is a further object of this invention to provide this protective coating by spraying a mixture of the pesticide, insecticide or repellent with a suitable monomer with spraying equipment which pressurizes the monomer to allow the monomer to be sprayed.

It is a further object of this invention in one of its preferred embodiments to provide the monomer in combination with a catalytic curing agent.

It is a further object of this invention in another of its preferred embodiments to provide the monomer as a masked isocyanate.

It is a further object of this invention in one of its preferred embodiments to provide the masked isocyanate monomer together with a catalyst which will cause the monomer to polymerize at a lower temperature.

It is a further object of the present invention to provide spraying equipment with a heating element which will unmask the isocyanate monomer and initiate a polymerization reaction.

It is a further object of this invention to provide pellets containing pesticide, insecticide or repellent bonded within a polymer matrix within the pesticide, insecticide or repellent/monomer mixture.

It is a further object of this invention to cause an exothermic reaction which causes the monomer to cross link and bond at a temperature below the temperature at which the pesticide, insecticide or repellent will become volatile or be degraded. It is a further object of this invention to protect humans and other desirable organisms from exposure to the pesticide, insecticide or repellent that are contained in the sprayed on monomer as well as degradation of these compounds with a second coating of ethylene vinyl acetate (EVA), polyvinyl alcohol (PVA), polyvinyl acetate latices, styrene butadiene latices, or like materials.

SUMMARY OF THE INVENTION

The present invention is a cost effective method for creating a barrier, or coating, whose properties prevent the infiltration of termites, ants, other wood boring insects and wood decaying microorganisms, which is conveniently applied to all forms of structures affected by such pests. The method for creating this coating involves spraying the structure with a quick setting liquid monomer. The monomer, when cured, will form a bonded polyurethane coating upon the surface of the item to be protected from the wood boring, destroying and/or decaying pests. This method of application provides a number of advantages over prior art methods of pest protection. For example, the present invention minimizes the amount of pesticide, insecticide or repellent, and uses the pesticide, insecticide or repellent at an optimum rate, thereby repelling pests for decades with a single application. Also, the pesticide, insecticide or repellent is essentially environmentally benign as it is effectively prevented from entering the environment in quantities which would cause concern. The present invention further allows an inexpensive and convenient method for applying pesticide, insecticide or repellent to both new and existing structures. Finally, the present invention produces additional benefits to the user such as allowing lower construction costs by reducing providing a moisture and radon barrier for new and existing structures.

As used herein, "polyurethane" is understood to include polyurethanes, polyureas, polyetherureas, polyisocyanurates, polycarbodiimides. Said polymers are prepared by polyaddition of nucleophiles (e.g., polyols, polyamines, water) to form polyisocyanates that contain two or more isocyanate groups, and combinations thereof. As used herein, the term "monomer" includes all substances that react to form polyurethanes. These monomers may themselves be polymers or "prepolymers" which contain multiple nucleophilic groups or isocyanate groups. Even water can be used to make these polymers and is in this sense a monomer. For example, when water is utilized in a reaction with a polyisocyanate to form a polyurea, it is included within the definition of monomers herein. The term monomer should also be understood to include blends of monomers.

Prior to, or concurrent with spraying, the monomer is mixed with a suitable pesticide, insecticide or repellent Suitable insecticides will impart its insect resistive properties to the coating. Acceptable insecticides include insecticides approved by the U.S. Environmental Protection Agency to kill or repel termites, ants, other boring insects and wood decaying microorganisms. The class of insecticide which is presently preferred for use in the present invention are pyrethrins, including tefluthrin, lambdacyhalothrin, cyfluthrin, deltamethrin, cypermethrin, permethrin, and natural permethrin. It will, however, be recognized by those skilled in the art that other effective insecticides such as isofenphos, fenvalerate, cypermethrin, permethrin, natural pyrethrin, organophosphate type insecticides, repellents as well as naturally occurring chemicals that act as irritants such as skunk oils and extracts of pepper can also be used. These are available from a number of commercial sources such as Dow, Mobay, ICI, Velsicol, Novartus, Zeneca and FMC respectively. Insecticides, pesticides, or repellents, alone or in combination with one and another, or in combination with other bioactive ingredients, such as fungicides, may also be used in accordance with the present invention, and as used herein, the terms "pesticides" should be construed to include all such combinations of insecticides, pesticides, repellents, nematicides (also referred to as nematocides), and fungicides. Fungicides include N-trihalomethythio, carboximide, dicarboximide, diflumetorim, ferimzone, chloropicrin, pentrachlorophenol, tri-chloronitromethane, 1-3dichloropropane, and sodium N-methyl dithiocarbomate. Nematicides include 1,3 dichloropropene, ethoprophos, fenamiphos, benfuracarb, and cadusafos.

In one preferred embodiment of the present invention, the pesticide/monomer mixture is provided as a single part delivery system. In a single part system, the pesticide is mixed with a "masked" isocyanate monomer, suitable nucleophiles, (e.g. Polyols and/or polyamines) and suitable catalysts (e.g. triethylene diamine and/or organotin compound. Dimerization of isocyanates with phosphine catalysts produces thermally reversible isocyanates. As used herein, "masked" isocyanates, also called "capped isocyanates" or "blocked isocyanates," refers to isocyanates that have been reacted with nucleophiles to prevent premature reaction with the nucleophiles that will form the product polyurethane. The masking agent may be removed by action of heat and/or catalyst that liberates the isocyanate group for reaction. Such masked isocyanates are well understood by those skilled in the art. For example, Oertel's Polyurethane Handbook discusses the use of phenols, caprolactam, oximes, triazoles, alcohols, and beta carbonyl compounds as appropriate masking agents, and the present invention should be understood to encompass such systems. U.S. Pat. No. 5,470,945, entitled Thermally Reversible Isocyanate-based Polymers to Markle et al. also describes one such masked isocyanate system.

Masked isocyanates are made to polymerize when the thermally weak bond formed by the masking agent is broken at higher temperatures, after which the polymerization proceeds rapidly. Thus, in the present invention, masked isocyanates are first mixed with a pesticide. A heating element that is part of the spraying equipment then heats the masked isocyanate/pesticide mixture prior to spraying to unmask the masked isocyanate and bring about the onset of polymerization. The mixture is then sprayed upon the structure or item to be protected whereupon it polymerizes to form a durable, cross linked coating with excellent wear resistance and long lived pest resistance.

Catalysts may also be added to these one part systems to lower the reaction temperature down to levels more easily tolerated by the pesticide. For example, a good catalyst will drop the reaction temperature of polymerization from about 160° C. to about 120° C. Suitable catalysts include homogeneous and heterogeneous catalysts. Heterogeneous catalysts are usually provided as fine powders. Examples of suitable catalysts include tertiary amines, organometallic tin compounds, triethylene diamine, dibutyl tin dilaurate, dibutylbis(laurylthio)stannate, dibutyltinbis (isooctylmercapto acetate), dibutyltinbis(isooctyl maleate), dimethylcyclohexylamine, and 1,8-diazabiscyclo[5,4,0] undec-7-ene (DBU).

In another preferred embodiment of the present invention, the pesticide /monomer mixture is provided as a two part system. The pesticide /monomer mixture is combined with a low temperature catalytic curing agent to cure the pesticide /monomer mixture and form the protective coating. This may be accomplished simply by spraying the item to be protected sequentially; first with the pesticide /monomer mixture and then with a low temperature catalytic curing agent. However, it is preferred that the pesticide/monomer mixture be combined with a low temperature catalytic curing agent in a single spray application.

To combine the pesticide/monomer mixture with the low temperature catalytic curing agent in a single spray application, the two are mixed together immediately prior to spraying, to prevent the clogging of the spray equipment. Preferably, the curing agent is combined with the pesticide/monomer mixture within the nozzle of a pressurized spraying device. However, applications wherein the pesticide/monomer mixture is combined with a low temperature catalytic curing agent prior to the introduction of the mixture into the spraying device are within the scope of the invention.

In a two part system, once the curing agent is in contact with the monomer, the curing agent initiates an exothermic chemical reaction which causes the monomer to the cross link and form a bonded urethane coating. Since elevated temperatures can cause undesirable effects with respect to the pesticide, it is important to select monomers and catalysts which will form the bonded urethane coating in a chemical reaction which proceeds at relatively low temperatures. At elevated temperatures, the pesticide may be volatilized, resulting in the release of the pesticide into the atmosphere where it may potentially harm the person operating the spraying equipment or other individuals in the vicinity of the spraying process. Also, elevated temperatures may degrade or damage the pesticide, causing it to lose its effectiveness in repelling or killing of insects or other pests. Thus, catalysts and monomer combinations which will cause the monomer in the pesticide /monomer mixture to cross link and bond in an exothermic reaction which will not exceed 140° F. are preferred. The most exothermic reactions occur with isocyanates and water, compared with alcohols or amines. Therefore, preferred combinations will minimize or exclude water, however, in certain cases where the pesticide is more labile and less volatile water may be used as a catalyst. Among the polyols, propylene oxide-based polyols are preferred as they will have lower exotherms than will ethylene oxide-based polyols. Amines are highly reactive in general, thus sterically hindered polyfunctional amines are preferred for the present invention. In general, aliphatic isocyanates are more reactive and have bigger isotherms than aromatic isocyanates. Thus, the use of steric hindrance is preferred as it and lowers the reaction temperatures to preferred levels. Oligomeric or polymeric polyisocyanates can also be useful.

Especially preferred is the use of prepolymers wherein much of the reaction between the isocyanate portion and polyol is conducted before the pesticide is introduced. This technique avoids a lot of problems associated with chemical attack and high exotherms.

A great variety of suitable spraying devices are suitable for the practice of the present invention. For example, pages 158–170 of Oertel's "Polyurethane handbook" published by Hanser in 1993 describe a variety of suitable mixheads. These devices are well understood by those having skill in the art, and no further elaboration of their operation is necessary to enable their use in the practice of the present invention. As contemplated by the present invention, any spraying device which will allow a liquid to be combined with pressurized gas (typically air) and expelled as a fine mist or droplet is acceptable, as are spraying devices which allow the delivery of liquid under pressure without air. When practicing the preferred embodiment of the present invention wherein the pesticide/monomer mixture and the catalyst is provided as a two part system, preferred spraying devices allow the curing agent to be combined with the pesticide/monomer mixture within the nozzle by allowing for the introduction of at least two liquid feed streams into the spraying nozzle.

Whether practicing the present invention as a one part system or two part system, especially preferred spraying devices also create highly turbulent conditions within the nozzle, ensuring good mixing of the curing agent and the pesticide/monomer mixture within the nozzle prior to spraying. In this manner, the curing agent is evenly dispersed throughout the pesticide/monomer mixture, ensuring even curing across the entire resultant coating. Due to the dangers associated with the pesticide, typically, the monomer is mixed with the pesticide in a controlled environment and the pesticide/monomer mixture is then utilized by workers operating mobile spray application equipment. In this manner, the pesticide is only brought into the field in a highly diluted form, greatly enhancing safety by greatly reducing the toxicity, and thus the consequences, of any spill. However, in some applications, it may be desirable to also combine the monomer and the pesticide, together with a curing agent if needed, as two or three separate liquid feed streams at the time of spraying. In these applications, it is preferred that the curing agent, the pesticide, and the monomer be combined within the nozzle and therein rendered in a highly turbulent state. In this manner, turbulent conditions within the nozzle insure that the pesticide is evenly dispersed throughout the resultant coating and is integral thereto.

It is preferred that the pesticide be evenly dispersed throughout the resulting coating. In this manner, the coating will impart resistance to insects or other pests throughout the surface area covered by the coating. In one preferred embodiment, it is preferred that the coating release the pesticide at a relatively rapid rate. By releasing the pesticide at a relatively rapid rate, the pesticide begins to repel unwanted insects immediately upon application. Preferably, the release rate of the coating is between about 0.01 and 15 $\mu g/cm^2/day$. For example a series of pesticides were formulated in accordance with the preferred methods described herein. Table 1 shows the resulting release rates for those various pesticides from the sprayable polyurethane.

TABLE 1

| Type & Percent by wt of Pesticide | Thermoset polymer | Initial Release Rate in μg/cm2/day | Steady State Release Rate μg/cm2/day |
|---|---|---|---|
| Chlorpyrofos - 5% | Sprayable Urethane | 9.7–15.1 | 0.73–2.65 |
| Permethrin - 5% | Sprayable Urethane | 4.7–7.9 | 0.91–2.91 |
| Lamdacyhalothrin - 5 | Sprayable Urethane | 0.56–1.98 | 0.03–0.27 |
| Deltamethrin - 5% | Sprayable Urethane | 3.76–4.79 | 1.93–2.78 |

Relatively large micropores are needed for the coating to have this property. This may be accomplished by providing the monomer in an emulsion. Removal of the more volatile component of the emulsion, known as "degassing" in the trade, leaves a urethane precipitate that has the other emulsion ingredient still present. Removal of that liquid may then generate tiny holes, or micropores, in the coating.

In one preferred embodiment of the present invention, pellets are added to the pesticide/monomer mixture. The pellets preferably are small enough to fit through the spray head of standard spraying equipment utilized in the practice of the present invention, or below about $1/16^{th}$ inch in diameter and comprise the same pesticide bound within polymer matrixes. Preferably, these pellets release pesticide at a relatively slow rate an are produced in a manner similar to that described in U.S. Pat. No. 5,856,271 to Cataldo et. al., the entire contents of which are incorporated herein by this reference. By releasing the pesticide at a relatively slow rate, the pellets continue to disperse pesticide into the polymer coating long after the pesticide originally within the pesticide/monomer mixture has dissipated. Preferably, the release rate of the pellets is the minimum level sufficient to replenish the pesticide in the polyurethane in an amount sufficient to continue to repel unwanted pests, or between about 0.1 and 8 $\mu g/cm^2$/day. To achieve these low release rates, the polymers utilized in these pellets are preferably selected from polyethylene and polypropylene or a porosity reducing agent to reduce the release rate.

The coatings thus formed by the practice of the present invention in its preferred embodiments will immediately begin releasing pesticide in sufficient quantities to deter the invasion of pests through the barrier formed by these coatings. These coatings will also continue to release pesticide in sufficient quantities to deter the invasion of pests for many years, in some cases for periods of thirty years or greater. To enhance the safety of these coatings, a protective layer of ethylene vinyl acetate (EVA), polyvinyl alcohol (PVA), or a like material may also be applied. The EVA is also applied as a sprayed coating utilizing spray equipment well known by those having skill in the art. The EVA is applied in a second spraying on top of the polyurethane coating that has cured. The EVA coating provides a protective barrier to prevent humans and other animals from coming into contact with the pesticide being released from the coating. The EVA coating also assists in enhancing the durability of the coating through its resistance to the effects of UV radiation.

In addition to EVA and PVA coatings, polyvinyl acetate latex coatings can be applied to the cured urethane product, using spray technologies employed to paint the interior of buildings. Copolymers of vinyl acetate with acrylic esters also are used to make latices that are promising for spray application.

Styrene butadiene latex paints also can be spray-applied to protect humans from contact with the pesticide. Whether these hydrophobic coatings or the above hydrophilic coatings are preferred depends on the solubility parameter of the pesticide. Hydrophobic coatings should be used with hydrophilic pesticides and vice versa.

The invention should in no way be limited to the specific examples set forth in these descriptions of the preferred embodiments; they are presented merely to illustrate preferred and acceptable methods of practicing the present invention. Further, while a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method for applying a barrier around structures to prevent the infiltration of pests including termites, ants, other wood boring insects, and wood decaying microorganisms, comprising the steps of:

a) providing a mixture of one or more monomers that react to form a polyurethane, a pesticide, and a pellet comprising a polymer and a pesticide, b) initiating the polymerization of the one or more monomers, c) directing the mixture through the nozzle of a pressurized spraying device, and d) spraying the mixture onto the structure.

2. The method of claim 1 wherein the polymerization of the monomer is initiated by combining said mixture with a low temperature catalytic curing agent.

3. The method of claim 2 wherein the catalytic curing agent is one or more of tertiary amines or organometallic tin compounds.

4. The method of claim 1 wherein the polymerization of the monomer provided is a masked isocyanate.

5. The method of claim 4 wherein the polymerization of the masked isocyanate monomer is initiated by heating the masked isocyanate monomer.

6. The method of claim 4 wherein the temperature of polymerization of the masked isocyanate monomer is reduced by the addition of a catalyst.

7. The method of claim 1 wherein the wherein the pesticide is selected from the group comprising pyrethrin, tefluthrin, lambdacyhalothrin, cyfluthrin, deltamethrin, isofenphos, fenvalerate, cypermethrin, and permethrin.

8. The method of claim 3, wherein said catalytic curing agent is selected from one or more of triethylene diamine, dibutyl tin dilaurate, dibutylbis(laurylthio)stannate, dibutyltinbis(isooctylmercapto acetate) dibutytinbis (isooctyl maleate), dimethylcyclohexylamine, or 1,8-diazabiscyclo[5,4,0]undec-7-ene.

9. The method of claim 1 wherein the polymer is selected from the group comprising polyethylene and polypropylene.

10. The method of claim 1 comprising the additional step of spraying an additional coating selected from the group ethylene vinyl acetate, polyvinyl alcohol, polyvinyl acetate latices and styrene butadiene latices onto the structure on top of the coating provided by the mixture and agent.

11. The method of claim 1 wherein the polymerization reaction proceeds to completion without reaching a temperature which will volatilize the monomer.

12. The method of claim 11 wherein the polymerization reaction proceeds to completion at a temperature of less than 140° F.

13. The coating formed by the method of claim 1.

* * * * *